United States Patent

Cooper

[11] Patent Number: 5,571,076
[45] Date of Patent: Nov. 5, 1996

[54] VERTICALLY-APPLIED SUPPORT FOR THE MUSCLES AND BONES OF THE VERTEBRAL COLUMN

[76] Inventor: Philip L. Cooper, 1700 Elizabeth St., Anniston, Ala. 36207

[21] Appl. No.: 390,293

[22] Filed: Jan. 23, 1995

[51] Int. Cl.$^6$ .................................................. A61F 5/00
[52] U.S. Cl. ................................................ 602/19; 2/44
[58] Field of Search ............................ 602/19; 128/873, 128/874; 2/44, 92; 450/155

[56] References Cited

U.S. PATENT DOCUMENTS

| | | | |
|---|---|---|---|
| 3,521,623 | 7/1970 | Nichols et al. | 602/19 X |
| 4,120,297 | 10/1978 | Rabischong et al. | 602/19 |
| 4,813,080 | 3/1989 | Toso | 2/44 X |
| 4,991,234 | 2/1991 | Greenberg . | |
| 5,127,897 | 7/1992 | Roller | 602/19 |
| 5,267,947 | 12/1993 | James et al. . | |
| 5,328,447 | 7/1994 | Kapounek et al. | 2/92 X |
| 5,349,706 | 9/1994 | Keer . | |
| 5,381,558 | 1/1995 | Lo | 2/92 X |

*Primary Examiner*—Linda C. Dvorak

[57] ABSTRACT

A body garment (FIG. 3) to which is attached extra vertebrae muscles (FIG. 1) comprised of: two half-rounds (4) containing pliable material fastened to a less pliable shroud (2). The shroud 2 captures the two half-rounds 4, thus making a two body contact on either side of the spinous process of the concave portion of the human back. Thus, making pressure contact with the erector spinae muscles on either side of the spinous process and on the outside of the transverse process, and on both sides of the spinous process. The erector spinae muscles and other muscles of the vertebral column help in lifting. However, their primary function is to protect the vertebrae bones, disks, and ligaments from slippage of a single vertebra, thereby preventing injuries to the surrounding ligaments and muscles. The body garment (FIG. 3) fasteners control body garment (FIG. 3) pressure to specific areas of the upper body. Fastening the waist fastener (8) and the upper abdominal fastener (10) will control body garment (FIG. 3) pressure to the extra vertebrae muscles (FIG. 1) and the lumbar back and abdominal muscles when lifting normal loads. For heavy lifting, the upper garment (12) and buttocks (14) fasteners are also used. Fasteners (8) (10) (12) are body wrap fasteners; buttocks fastener (14) is used for cupping the body garment (FIG. 3) for heavy lifting. The cupping of the body garment (FIG. 3) provides vertical vertebrae pressure support that increases as the wearer bends to lift. When fastening the body garment for heavy lifting, the voids in support to the vertebrae will be filled with bulk support pressure by the extra vertebrae muscles (FIG. 1), even when twisting and bending awkwardly. The extra vertebrae muscles (FIG. 1) will give vertical support to the vertebral column. The body garment will give the upper body muscles of the back and abdomen pressure support controlled by the fasteners.

5 Claims, 1 Drawing Sheet

5,571,076

VERTICALLY-APPLIED SUPPORT FOR THE MUSCLES AND BONES OF THE VERTEBRAL COLUMN

BACKGROUND

CROSS-REFERENCE TO RELATED APPLICATIONS

This invention uses similar material and design to my invention application included in this package, entitled Contoured Therapeutic Spinal Support.

1. Field of Invention

This invention relates to support of the back when lifting, specifically by providing vertical bulk pressure support to the vertebrae bones and muscles.

2. Description of Prior Art

Devices for support of the back, particularly for manual lifting, have been on the market for several years. According to industry estimates, there are currently about 50 manufacturers of back support belts. The belts come in an array of styles, materials and color yet, they are all similar in design and function. They compress the abdomen and become uncomfortable if a worker twists in a hazardous posture to pick up a heavy object. Naturally, the description provided by each manufacturer suggests that their belt is best.

However, an agency of the U.S. Government has called into question the current effectiveness of back support belts. A working group of the National Institutes of Occupational Safety and Health (NIOSH) concluded In a study report released in July 1994 that there was inconclusive scientific evidence that back belts actually reduce the risk of back injuries in workers.

Manufacturers and industry group have disputed the NIOSH findings. Medical practitioners have joined the fray, largely in support of the NIOSH report. However, there seems to be widespread agreement that further study is needed. This is after the NIOSH working group analyzed 21 earlier studies as to the effectiveness of back belts.

My contention is, after 21 studies and the recommendation that more study is needed, that the problem may be that everyone is trying to make the current design of back support belts work as claimed, instead of looking at the human body for answers, While the physiology of the human body is ample for lifting of weight, human nature is such that workers will invariably try to lift more tan the body can support and/or lift in an awkward, twisting manner that exceeds what the human muscular-skeletal frame can support without exposing vertebrae bones an tissue to inadequate, strained muscular protection. The NIOSH report recommends increased implementation of ergonomics programs. This is a worthy venture but one that ideally assumes that workers caught in the daily routine of workplace demands, time pressures, and distractions will conform to ergonomically-correct guidelines.

Current designs of back support belts act as an abdominal and back brace, but do not:

(a) Adjust and conform to the vertical design of the human vertebral column, (b) Provide direct compensating muscular support to vertebrae bones and tissues as the back twists, bends and stretches during lifting.

Facts, History and Theory

There are many man-hours of work lost due to back injuries that occur when lifting. Such injuries take an additional toll in medical claims and human suffering.

Because of the undisciplined work force in the art of correct lifting and the inability of existing back support belts to reduce back injuries, it is time for a new look at the source of injuries and why they occur.

Many lifting injuries occur when the load is too heavy and the lifting is made while bending and/or twisting awkwardly, using either the right or left side. Lifting muscles are seldom injured, but they cause injuries to the protective muscle of the vertebral column and the disk of the vertebrae.

In the structure of the vertebral column each vertebra is separated by a disk of cartilage. Three projecting bones, the spinous process and the transverse process on either side of the spinous process, are important component of each vertebra, as these processes serve as muscle attachments.

Along both sides of the spinous process and on the outer side of the transverse processes lie the erector spinae muscles that support lateral movement. The major and minor psoas fascia muscles are also attached to the inside of the transverse processes. These muscles help in lifting by allowing the vertebral column to bend.

However, the primary purpose of these and other muscles of the vertebral column are to protect the vertebrae by bulk muscle support for the bones, disks, and ligaments of the vertebral column.

It is said that recognition of a problem is 90 percent of the solution. The manufacturers of the back support belts have not recognized the problems in supporting the back when lifting.

I think I have identified two problems. First, the lifting muscles are seldom the ones injured when lifting. They cause injuries, especially when someone is lifting incorrectly. Second, the vertebral column, which may be described as being to the human body what the boom is on a construction crane, is the recipient of most injuries caused by lifting.

Basically, there are three lifting positions for our vertebrae crane boom—straight on lift, right side lift, left side lift. By means of example, in an extreme lift or pull to the right side, the left side muscles of the vertebrae boom are stretched thin. They are not bulky enough to completely support the left side of the vertebrae against the thrust of the more bulky, contracted, rigid muscles of the right side. During the physical act of lifting or pulling, the interaction of back muscles combined with body twists will place the fulcrum of the load largely on the area of one vertebra. This dramatically increases the likelihood of injury because there is not enough bulk muscle support to the vertebrae on the left side to prevent strain or other injury to the disks, muscles, or ligaments.

I have fashioned a firm but pliable device that I am describing as extra vertebrae muscles. This apparatus is designed to straddle the spinous process and place bulk pressure on the erector spinae muscles from the sacrum through the lumbar and into the lower thoracic vertebrae. The extra vertebrae muscles device is attached to a body garment that can be fastened in several key areas of the human torso.

Objects and Advantages

Accordingly, besides the objects and advantages of the extra vertebrae muscles device mentioned in the above paragraph, the objective of the extra vertebrae muscles are to stabilize the vertebral column as one single unit by applying vertical pressure to the erector spinae muscles on either side of the spinous process. In so doing, the extra vertebrae muscles provide increasing pressure and bulk muscle support to the vertebral column, particularly the side opposite the lift flow is more vulnerable to injury.

This vertically applied bulk pressure support is applied by means of a body garment and fasteners that can be easily adjusted to either increase or decrease support pressure as needed for lifting, pulling, or other physical activity that places strain on the vertebral column. Use of the body garment fasteners will also provide means for attaching support for muscles and bones to specific locations of the upper body.

The extra vertebrae muscles attached to the body garment will give support pressure to the erector spinae muscles as the wearer bends and twists at the same time. When this or similar forms of exertion creates voids in vertebrae protection, the pressured pliable extra vertebrae muscles will fill the voids by bulk and by increasing pressure on the vertebrae muscles from the sacrum to the lower thoracic vertebrae. The spinous process is captured between the two half-rounds of the extra vertebrae muscles, thereby helping to prevent the vertebral column from twisting.

DRAWING FIGURES

Figure 1:
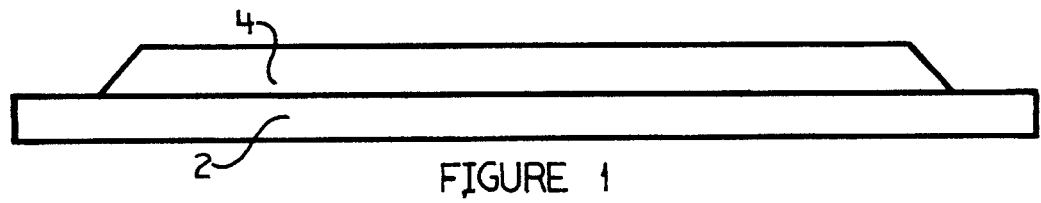
FIG. 1 shows a profile of the extra vertebrae muscles
Figure 2:
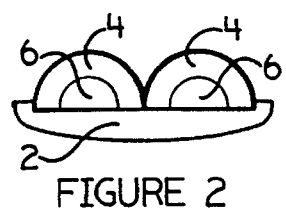
FIG. 2 shows a section view of the extra vertebrae muscles

REFERENCE NUMERALS IN DRAWINGS 2 shroud of extra vertebrae muscles 4 half-rounds of extra vertebrae muscles 6 space to allow collapsing of half-rounds to provide wider support coverage 8 waist fastener 10 upper abdominal fastener 12 upper body garment fasteners 14 buttocks fastener 16 extra vertebrae muscles location fastener

DESCRIPTION

Two half-rounds 4 of pliable material fastened to a less pliable shroud 2, thus making a one piece (FIG. 1) two body contacts on either side of the spinous process of the concave portion of the human back. This makes pressure contact with the erector spinal muscles on either side of the spinous process, and on the outside of the transverse process on both sides of the spinous process.

The extra vertebrae muscles (FIG. 1) will have collapsing space 6 to allow for wider coverages.

The extra vertebrae muscles (FIG. 1) will apply bulk support pressure vertically to the vertebrae from the sacrum to the lower thoracic vertebrae.

Figure 3:
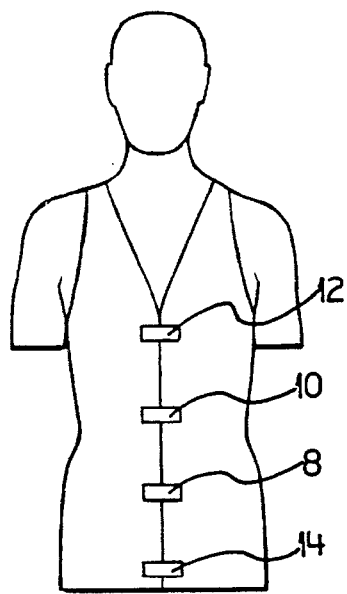
FIG. 3 shows front view of body garment and locations of fasteners
Figure 4:
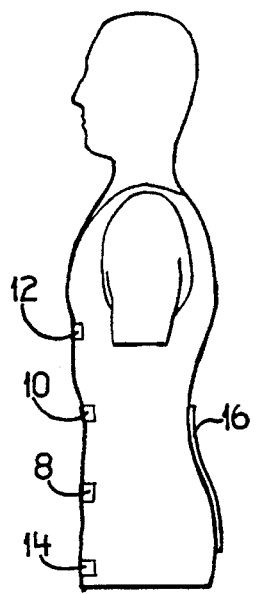
FIG. 4 shows side view of body garment and locations of fasteners and placement of the extra vertebrae muscles.
Figure 5:
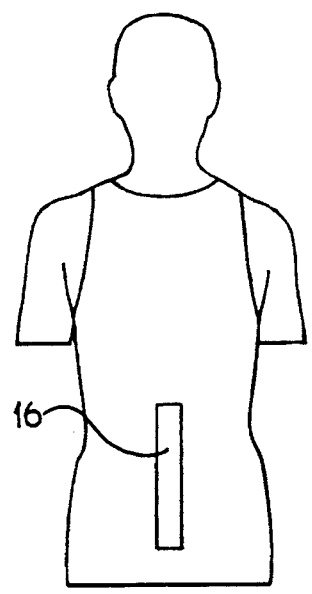
FIG. 5 shows back view of body garment and placement of the extra vertebrae muscles.

The shroud 2 of the extra vertebrae muscles (FIG. 1) will be fastened to a body garment by means of fasteners 16. The body garment (FIG. 3) will be fashionable and can take the appearance of many types of upper body clothing that could conceal the extra vertebrae muscles (FIG. 1). The garment will have holes for the arms and will be fastened by fasteners attached to the garment.

The body garment (FIG. 3) fasteners at the waist 8 and upper abdominal area 10 will control body garment (FIG. 3) pressure to the extra vertebrae muscles (FIG. 1) and lumbar back and abdominal muscles at the same time. This is the designed fastening for light and normal lifting.

For heavy lifting the body garment (FIG. 3) will be fastened at the waist 8, the upper abdominal area 10, the upper garment (FIG. 3) fastener 12, and the buttocks 14.

Fasteners 8, 10, 12, are body garment wrap fasteners. Fastener 14 at the buttocks gives vertical vertebral column support from the sacrum through the thoracic vertebrae. This will include the extra vertebrae muscles (FIG. 1) in the lumbar and lower thoracic section of the vertebral column.

Operations

Two workers prepare to unload a truck of different sized boxes weighing from 40 to 70 pounds. One worker is in the truck while the other stands on the ground. Both workers are wearing the body garment (FIG. 3) with the extra vertebrae muscles (FIG. 1) fastener 16.

Both workers will fasten all lifting fasteners, including the waist 8, the upper abdominal 10, the upper garment (FIG. 3) fastener 12, and the buttocks cupping fastener 14.

The worker in the truck reaches up high to get the top box. The waist fastener 8 and upper abdominal fastener 10 will keep firm pressure on the extra vertebrae muscles (FIG. 1) 16, which will, in turn, keep constant firm pressure on the erector spinae muscles on both sides of the spinous process as well as the spinous process. As the worker twists and bends to lift a 70 pound box and set it down, rapid muscular changes occur in the vertebrae and body muscles. When muscles contract when lifting the opposing muscles must relax. This rapid contracting, relaxing, recontracting places tremendous pressure on the vertebra that receives the most strain in a given instance.

In the above action, the extra vertebrae muscles (FIG. 1) were filling the voids created by the contracting, relaxing, and recontracting of the vertebrae muscles by means of pliable, resilient, bulky material that follows every movement of the erector spinae muscles. This was giving support to the vertebral bones as well.

The worker on the ground has a similar muscular cycle of lifting the 70 pound box up from the edge of the truck and then turning to set it down onto a conveyor belt. This turning to either the right or left side will partially twist each vertebra. In a right side lift, the left side erector spinae muscles are reduced in bulk size as they stretch to follow the bend to the right side. This exposes the ligaments, disks, bones, and muscles. Without bulk muscle support the vertebrae disks and bones are much more vulnerable to injury. The extra vertebrae muscles (FIG. 1) are designed to give firm bulk support to these voids 4 in covering the bones of the vertebrae. This should greatly reduce the likelihood of an injury.

When break time arrives, both workers unfasten the buttocks fastener 14, the upper garment (FIG. 3) fastener 12, and the upper abdominal fastener 10. The waist fastener 8 remains fastened. This will give support to the vertebral column when sitting, standing, walking or doing light lifting. When the workers sit to relax the extra vertebrae muscles (FIG. 1) 16 become a back support that rests the vertebral column, with or without a backrest where they are seated.

Summary, Ramifications, and Scope

Accordingly, the reader will see that the extra vertebrae muscles attached to the body garment can be an advantage in support to the muscles of the spinal column and upper body.

Some of the advantages:

- the body garment to which the extra vertebrae muscles is attached controls by means of the location of the garment fasteners the part of the body that needs help;
- for light lifting, walking, or sitting, the extra vertebrae muscles will give bulk pressure support when the waist fastener is fastened;
- when fastening the upper abdominal garment fastener, the muscles of the thoracic, back, and abdomen are given pressure support;
- when lifting heavy loads requiring bending or twisting, both the upper garment fastener and buttocks cupping fastener are fastened, giving vertical support pressure to the extra vertebrae muscles by filling bulk support to voids in muscle relaxation;
- the amount of pressure given to any fastener is controlled by the user.

Ramifications—other embodiments of this invention

- in a situation where a person has sustained a serious spinal injury, emergency paramedics could use the body garment, with a full length vertebral column support attached to the body garment, to raise the injured vertebral column to its normal S-curve position prior to transporting the patient to a hospital or other emergency medical facility. Having the vertebral column in alignment near its normal position during transport should greatly reduce swelling and compression of the vertebrae, thereby decreasing the likelihood of paralysis or permanent disability. By contrast, in today's art the patient is typically strapped down in an unnatural, strained position for transport. On arrival, the attending medical personnel may have to reposition some vertebrae through the swelling and compressing of the vertebrae, causing further injuries or paralysis;
- sufferers of osteoporosis, osteoarthritis, or other spinal conditions could use the full body S-curve of the normal vertebral column support attached to the body garment. This would raise the lumbar vertebrae, thereby providing back support by relieving compression of the vertebral column;
- the portion of the body garment fastened at the waist for light lifting could be cut away to fashion a lumbar vertebrae support when sitting, standing, or walking. This could be used at work, during leisure activities, and in particular as a backrest when seated in a car;
- the extra vertebrae muscles could become a fashion object. By using different colors and fashion attachments, it could be worn discreetly on the outside of clothing to provide support to the back and vertebral column Although the description above contains many specifities, these should not be construed as limiting the scope of the invention but as merely providing illustrations of some of the presently preferred embodiments of this invention. For example, the extra vertebrae muscles could have other shapes—flat, round, two pieces separated by other material, foam supported by bands of flexible materials, etc.

Thus, the scope of the invention should be determined by the appended claims and their legal equivalents, rather than by the examples given.

I claim:

1. An upper torso garment having an integral support device for supporting the muscles adjacent to the vertebral column of a user while lifting said garment including a front panel and a rear panel and openings to accommodate the arms of the user wherein the improvement comprises:

an integral support device consisting of two parallelly adjacent lengths of half-rounded pliable material fastened by their flat sides to a less pliable shroud and fastened to the upper torso garment in such a way as to cause the rounded side of the pliable members to be in contact with the spinous process of the concave portion of the human back and make pressure contact with the erector spinal muscles on either side of the spinous process and on the outside of the transverse process on both sides of the spinous process;

said torso garment made of non-stretch material with means to be fastened in such a way as to maintain the integral support device in contact against the erector spinal muscles.

2. The upper torso garment of claim 1 in which the two parallelly adjacent lengths of half-rounded pliable material are hollow.

3. The upper torso garment of claim 1 in which said shroud is shaped to conform to the shape of a normal spinous process.

4. The upper torso garment of claim 1 in which said garment is fastened with a multiplicity of evenly spaced fasteners.

5. The fasteners of claim 4 situated in such a way as to allow the user to fasten only the bottom situated fasteners for light duty.

* * * * *